US009622931B2

(12) United States Patent
McKeeman

(10) Patent No.: US 9,622,931 B2
(45) Date of Patent: Apr. 18, 2017

(54) PORTABLE HYPERBARIC CHAMBER WITH A VERTICAL MOUNTING SYSTEM

(71) Applicant: Bruce Elgin McKeeman, Mound, MN (US)

(72) Inventor: Bruce Elgin McKeeman, Mound, MN (US)

(*) Notice: Subject to any disclaimer, the term of this patent is extended or adjusted under 35 U.S.C. 154(b) by 722 days.

(21) Appl. No.: 14/107,180

(22) Filed: Dec. 16, 2013

(65) Prior Publication Data

US 2014/0366881 A1    Dec. 18, 2014

Related U.S. Application Data

(60) Provisional application No. 61/835,303, filed on Jun. 14, 2013.

(51) Int. Cl.
*A61G 10/02* (2006.01)
*A61M 16/20* (2006.01)
*A61M 16/00* (2006.01)

(52) U.S. Cl.
CPC .......... *A61G 10/026* (2013.01); *A61M 16/20* (2013.01); *A61M 16/209* (2014.02); *A61M 2202/0208* (2013.01)

(58) Field of Classification Search
CPC ........ A61M 16/209; A61M 2202/0208; A61G 10/005; A61G 10/006; A61G 10/007; A61G 10/023; E04H 15/58; E04H 15/06; E04H 15/344
USPC ....... 52/2.18, 19, 69; 135/148, 900; 251/206
See application file for complete search history.

(56) References Cited

U.S. PATENT DOCUMENTS

| | | | | |
|---|---|---|---|---|
| 4,974,829 A * | 12/1990 | Gamow | ............... | A61G 10/026 128/200.12 |
| 5,467,764 A * | 11/1995 | Gamow | ............... | A61G 10/026 128/200.24 |
| 5,678,543 A * | 10/1997 | Bower | ................... | A62B 31/00 128/202.12 |
| 6,016,803 A * | 1/2000 | Volberg | ............... | A61G 10/026 128/202.12 |
| 6,845,781 B1 * | 1/2005 | Brown | .................... | B32B 27/12 135/116 |
| 7,263,995 B2 * | 9/2007 | Gurnee | ................ | A61G 10/026 128/202.12 |
| 8,025,056 B2 * | 9/2011 | Lewis | .................... | A62B 31/00 128/202.12 |
| 2009/0217930 A1 * | 9/2009 | Holley | .................... | E04B 1/166 128/205.26 |
| 2010/0059059 A1 * | 3/2010 | Evans | .................. | A61G 10/026 128/205.26 |

* cited by examiner

*Primary Examiner* — Justine Yu
*Assistant Examiner* — Douglas Sul

(57) ABSTRACT

A portable hyperbaric chamber with a vertical mounting system includes an inflatable enclosure which is vertically positioned by a rigid base. An internal frame also functions as an additional mounting system so that the inflatable enclosure can be vertically positioned during pressurized and not pressurized instances. A plurality of fill valves allows the inflatable enclosure to be pressurized from externally positioned compressors, and the inside pressure of the inflatable enclosure is measured and displayed through a pressure gauge. The inside pressure can be controlled from a dump valve, a low pressure relief valve, and a high pressure relief valve so that the proper operating pressure can be maintained with the hyperbaric chamber.

12 Claims, 19 Drawing Sheets

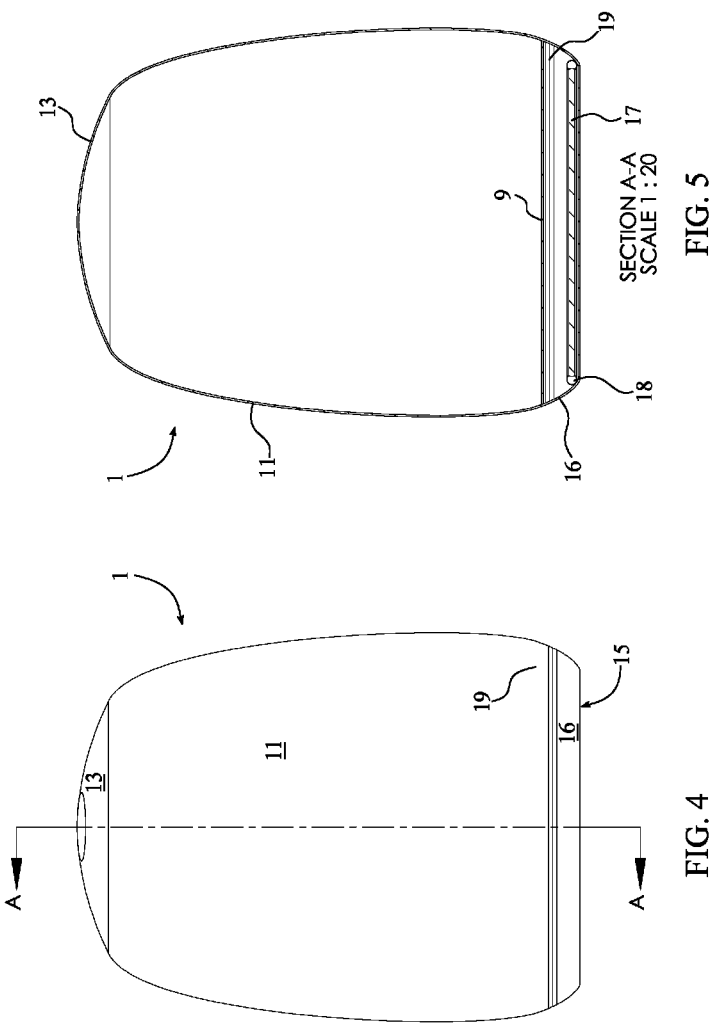

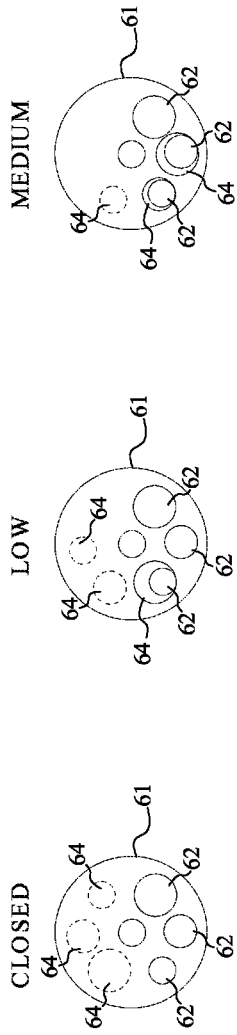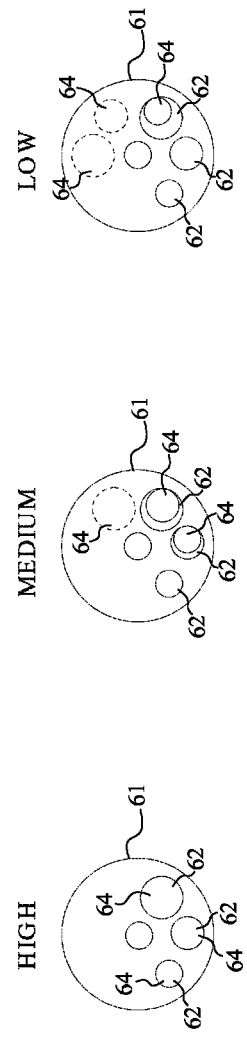

PORTABLE HYPERBARIC CHAMBER WITH A VERTICAL MOUNTING SYSTEM

The current application claims a priority to the U.S. Provisional Patent application Ser. No. 61/835,303 filed on Jun. 14, 2013.

FIELD OF THE INVENTION

The present invention relates generally to an apparatus and method for the creation of a vertical mild portable hyperbaric chamber. More specifically, the present invention creates a hard base and a frame to allow the portable hyperbaric chamber to stand upright with a flat solid floor. This allows occupants the unique opportunity to sit in a common chair inside on the chamber versus having to lie down.

BACKGROUND OF THE INVENTION

Hyperbaric chambers are commonly used in field of diving and hyperbaric medicine. Hyperbaric chambers are pressurized vessels designed for human occupancy, and can be designed with either a soft shell or hard shell construction. The act of confinement within a chamber can cause or exacerbate claustrophobia and or discomfort.

Because of the claustrophobic effect or the difficulty or impossibility of some patients to lie down, other methods have been used such as a Hoyer lift for those patients who have trouble lying down and physician support or calming medication for claustrophobia. However these methods have drawbacks of expense, inconvenience and embarrassment. In general there is no solution to the problem of inability to lie down in a mild portable hyperbaric chamber.

It is therefore an object of the present invention to provide an alternate to having to lie down to receive a hyperbaric treatment in a mild portable hyperbaric chamber. The present invention accomplishes this by creating a sleeve at one end of the chamber. A round floor with a protective highly friction resistant coating is introduced into the sleeve. The chamber will then inflate in an upright configuration allowing an individual to sit in a comfortable chair or stand in the chamber.

BRIEF DESCRIPTION OF THE DRAWINGS

FIG. 4 is a side view of the present invention, showing the plane upon which a cross sectional view is taken shown in FIG. 5.

FIG. 5 is a cross section view of thereof taken along line A-A of FIG. 4, showing the floor, the rim, and the inner carpet.

FIG. 11-A is a basic inside view of the dump valve which shows the plurality of stationary holes and the plurality of rotary holes are completely sealed from one another, wherein the dump valve is completely sealed.

FIG. 11-B is a basic inside view of the dump valve which shows the plurality of stationary holes and the plurality of rotary holes are partially sealed from one another, wherein the dump valve allows a small amount of air to escape.

FIG. 11-C is a basic inside view of the dump valve which shows the plurality of stationary holes and the plurality of rotary holes are partially sealed from one another, wherein the dump valve allows a large amount of air to escape.

FIG. 11-D is a basic inside view of the dump valve which shows the plurality of stationary holes and the plurality of rotary holes are completely aligned with one another, wherein the dump is working at its full capacity.

FIG. 11-E is a basic inside view of the dump valve which shows the plurality of stationary holes and the plurality of rotary holes are partially sealed from one another, wherein the dump valve allows a large amount of air to escape.

FIG. 11-F is a basic inside view of the dump valve which shows the plurality of stationary holes and the plurality of rotary holes are partially sealed from one another, wherein the dump valve allows a small amount of air to escape.

DETAIL DESCRIPTIONS OF THE INVENTION

All illustrations of the drawings are for the purpose of describing selected versions of the present invention and are not intended to limit the scope of the present invention.

Figure 1:
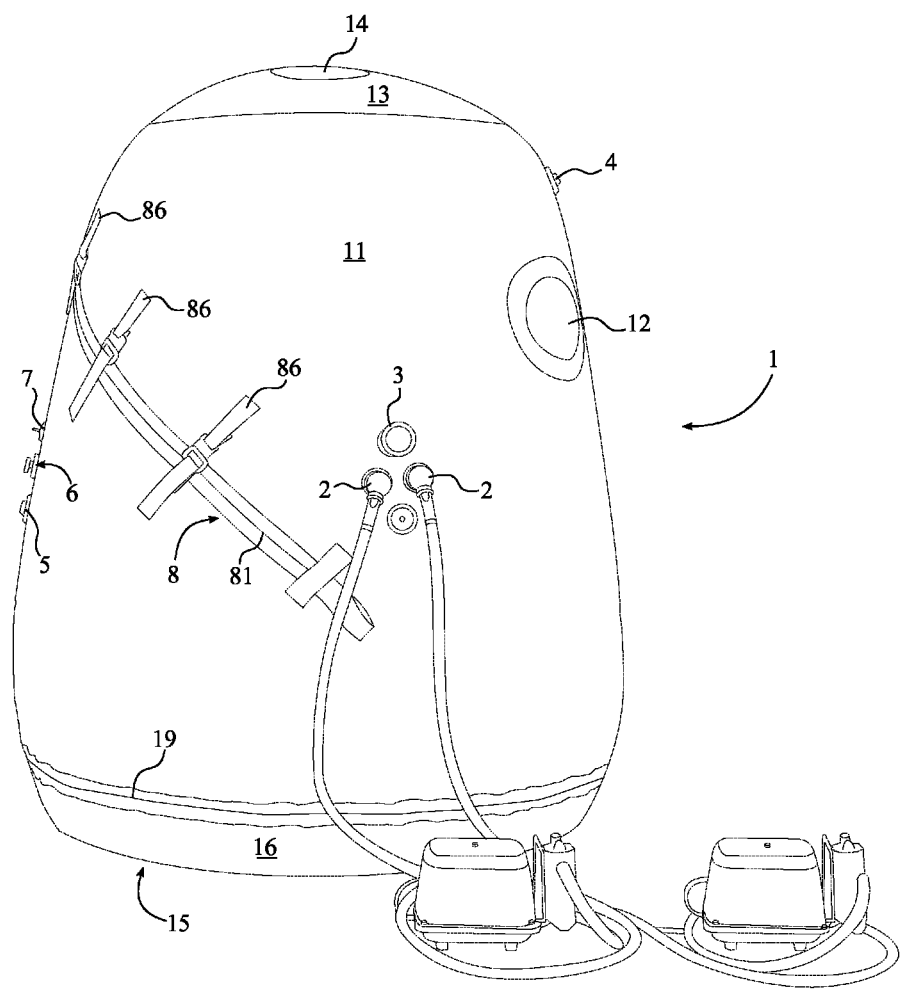
FIG. 1 is a front view of the preferred embodiment of the present invention with attached compressors, wherein the inflatable enclosure is pressurized.
Figure 2:
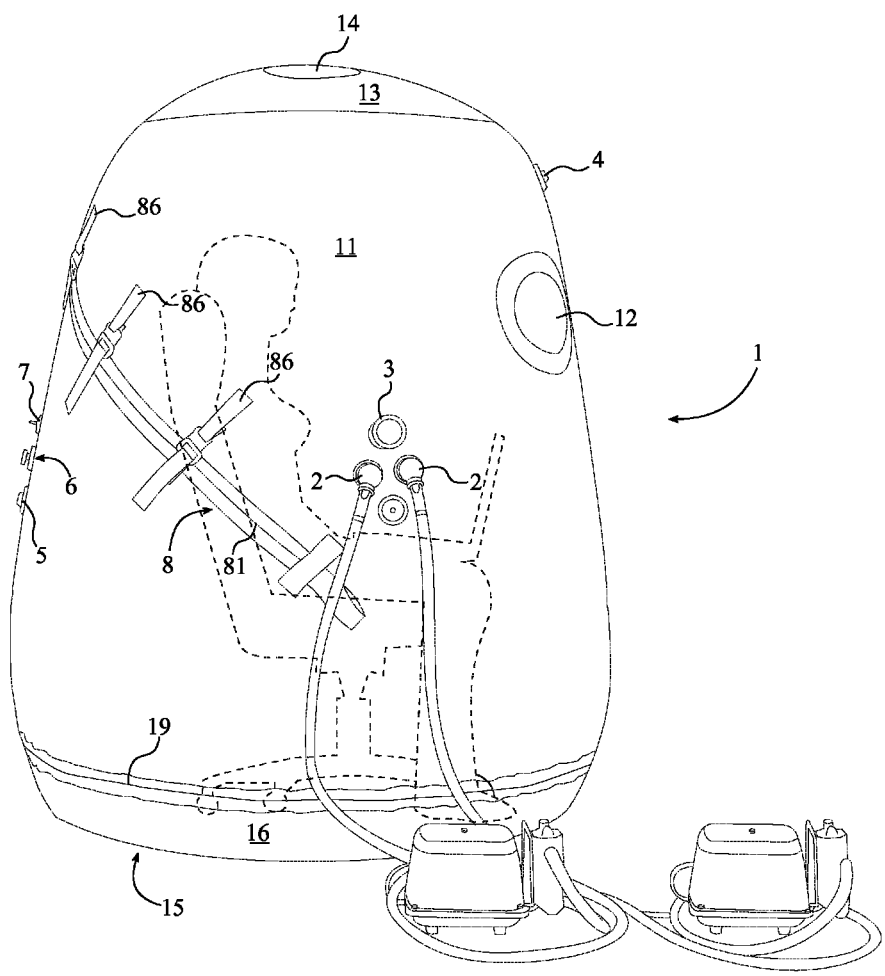
FIG. 2 is a front view of the preferred embodiment of the present invention with attached compressors, wherein the inflatable enclosure is pressurized and the dash lines show a patient sitting on a chair.

In reference to FIG. 1 and FIG. 2, the present invention is a portable hyperbaric chamber with a vertical mounting system, where the present invention comprises an inflatable enclosure 1, a plurality of fill valves 2, a pressure gauge 3, a low pressure relief valve 4, a high pressure relief valve 5, a dump valve 6, at least one auxiliary valve 7, an access opening 8, an inner carpet 9, and an internal frame 10. The components and their configurations of the present invention allow a patient to comfortably sit in a chair or a stand during the medical treatments as the chair or the stand can be placed within the present invention.

In reference to FIG. 1-FIG. 5, the inflatable enclosure 1 comprises a collapsible lateral wall 11, a roof panel 13, and a rigid base 15. The inflatable enclosure 1 is a pressurized vessel which creates a controlled environment so that the patients can sit in the chair or the stand during the medical treatments. The inflatable enclosure 1 is preferably made into a cylindrical shape, but is not limited only to the cylindrical shape and can be any other geometrical shapes. The collapsible lateral wall 11 is perimetrically connected around the rigid base 15 and the roof panel 13 in such way that the collapsible lateral wall 11 is positioned in between the rigid base 15 and the roof panel 13. The connections between the collapsible lateral wall 11, the roof panel 13, and the rigid base 15 are completed with the radio frequency (RF) welding so that the present invention can be completed with the high strength connection points for additional durability. The roof panel 13 comprises a first transparent window 14, where the first transparent window 14 is concentrically positioned on the roof panel 13 so that the light can enter into the inflatable enclosure 1 through the first transparent window 14. The collapsible lateral wall 11 comprises a second transparent window 12, and the second transparent window 12 is positioned on the collapsible window. The second transparent window 12 also allows the light to enter into the inflatable enclosure 1 and provides an outside view for the patient within the inflatable enclosure 1. In reference to FIG. 4 and FIG. 5, the rigid base 15 comprises a base sleeve 16, a floor 17, and a rim 18. The rim 18 is perimetrically connected around the floor 17, where the floor 17 and rim 18 are removably positioned within the base sleeve 16 through a base opening 19. The floor 17 provides the stiffness to the rigid base 15 while the rim 18 provides a smooth outer texture which minimizes the friction in between the rim 18 and the base sleeve 16 so that the floor 17 can be safely positioned within the base sleeve 16. The floor 17 and the rim 18 can be made from rigid and high strength materials including, but is not limited to, wood, plastic, metal, and any combination thereof. The floor 17 and the rim 18 are concentrically positioned with the base sleeve 16 to prevent tilting of the inflatable enclosure 1. The base opening 19 circumferentially extends around the base sleeve 16 so that the floor 17 and the rim 18 can be easily inserted through the base opening 19. The base opening 19 opens and closes through a fastening mechanism such as a zipper, a magnetic fastener, hook-and-loop fastener, and any other similar fastening mechanism.

Figure 6:
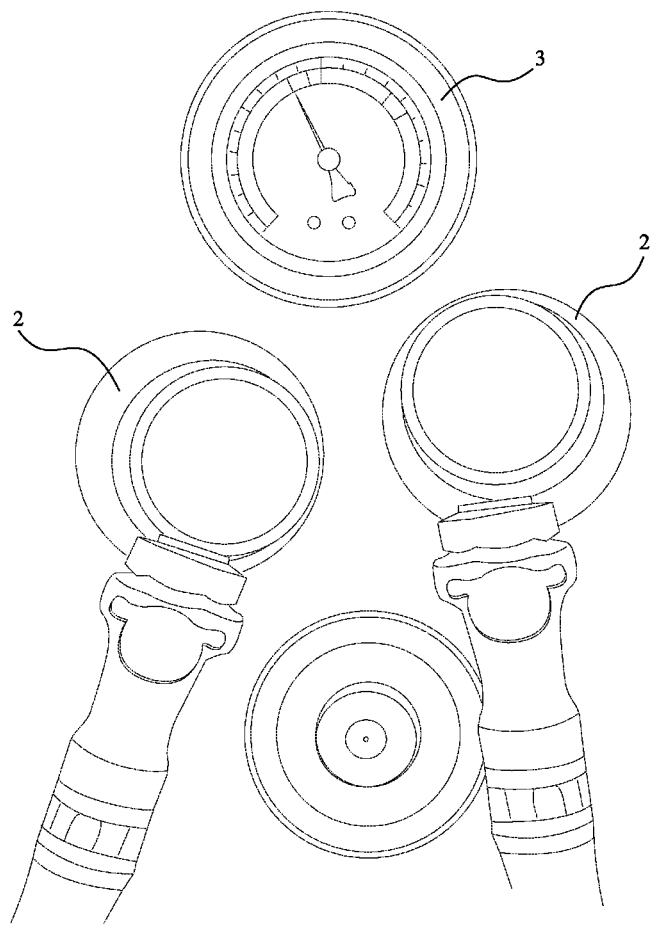
FIG. 6 is a detailed view of the plurality of fill valves and the pressure gauge of the present invention.
Figure 7:
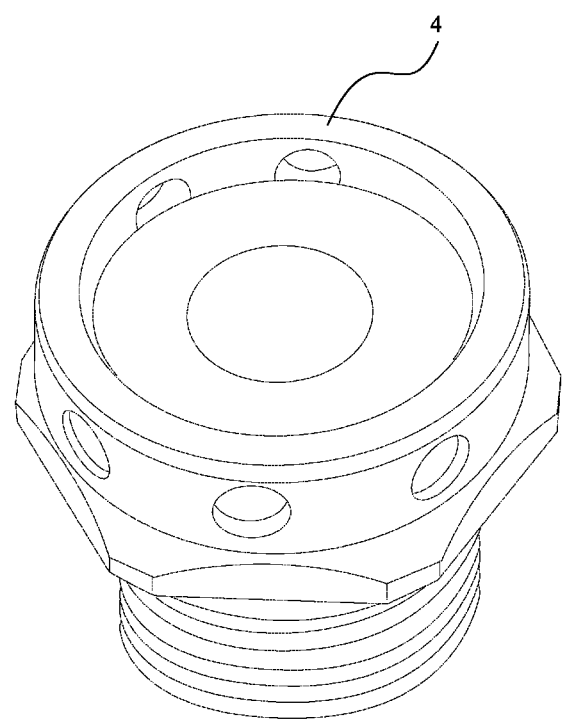
FIG. 7 is a detailed view of the low pressure relief valve of the present invention.

In reference to FIG. 1 and FIG. 6, the plurality of fill valves 2 is externally connected to the collapsible lateral wall 11 in such way that the plurality of fill valves 2 is traversed through the collapsible lateral wall 11. The plurality of fill valves 2 is able to provide fresh air into the inflatable enclosure 1 through compressors so that the inflatable enclosure 1 can be pressurized. More specifically, the each of the plurality of fill valves 2 is fluidly connected with a compressor by a medical grade tube as the medical grade tube comprises a quick-disconnect fitting at the first extremity and a standard fitting at the second extremity. The quick-disconnect fittings of the medical grade tubes snap into the plurality of fill valves 2 and the standard fittings connect with the respective compressors so that the fresh air from the compressors can be pumped in to the inflatable enclosure 1 through the medical grade tubes and the plurality of fill valves 2. The fluidly connected compressors of the present invention must remain in the on-position for the entire treatment period to ensure the proper circulation and exchange of fresh air so that a safe and comfortable environment can be obtained for the patient. Additionally, each of the plurality of fill valves 2 comprises a built-in muffler to reduce the noise of fresh air entering the inflatable enclosure 1 and a removable air filter to further purify the fresh air entering the inflatable enclosure 1.

In reference to FIG. 1 and FIG. 6, the pressure gauge 3 is externally connected to the collapsible lateral wall 11 in such way that the pressure gauge 3 is traversed through the collapsible lateral wall 11. The pressure gauge 3 of the present invention can be a mechanical pressure gauge or an electronic pressure gauge as both of them provides the same functionality. The pressure gauge 3 continuously measures the inside pressure of the inflatable enclosure 1 and displays through a display screen of the pressure gauge 3. The display screen is preferably color-coded for simplified reading, where the numerical pressure value is displayed with accuracy of a plus or minus five percent. More specifically, a first color of the display screen along with the numerical values indicates that the pressure within the inflatable enclosure 1 is below the operating pressure. A second color of the display screen along with the numerical values indicates that the inflatable enclosure 1 is at the operating pressure. A third color of the display screen along with the numerical values indicates that the inflatable enclosure 1 is above the operating pressure. Due to the different colors and their respective pressure ranges, the users of the present invention can easily monitor the operating pressure of the inflatable enclosure 1. The present invention may also comprise an optional internal pressure gauge, which functions similar to external pressure gauge 3, so that the inside pressure of the inflatable enclosure 1 can be displayed within the inflatable enclosure 1 for the patient within.

In reference to FIG. 1, FIG. 7, FIG. 8 and FIG. 9, the low pressure relief valve 4 and the high pressure relief valve 5 are externally connected to the collapsible lateral wall 11 in such way that the low pressure relief valve 4 and the high pressure relief valve 5 are traversed through the collapsible lateral wall 11. Both the low pressure relief valve 4 and the high pressure relief valve 5 allow the circulation of fresh air within the inflatable enclosure 1 and the expulsion of carbon-dioxide out of the inflatable enclosure 1 while maintaining the constant operating pressure within the present invention. The low pressure relief valve 4, which is preferably positioned toward the top end of the collapsible lateral wall 11, automatically opens once the inflatable enclosure 1 is fully pressurized in order to maintain the proper operating pressure. When the low pressure relief valve 4 is opened, circulated air within the inflatable enclosure 1 exits through the low pressure relief valve 4 and allows fresh air to enter into the inflatable enclosure 1. The low pressure relief valve 4 also maintains the operating pressure of the present invention. The high pressure relief valve 5, which is preferably positioned toward the middle of the collapsible lateral wall 11, automatically opens once the inflatable enclosure 1 is over pressurized with respect to the operating pressure. When the high pressure relief valve 5 is opened, circulated air within the inflatable enclosure 1 exits through the high pressure relief valve 5 while allowing fresh air to enter into the inflatable enclosure 1 and lowers the pressure within the inflatable enclosure 1 to the operating pressure of the present invention. Additionally, the low pressure relief valve 4 and the high pressure relief valve 5 are color-coded to match the second color and the third color of the pressure gauge 3 so that the users are able to differentiate the low pressure relief valve 4 apart from the high pressure relief valve 5. More specifically, the low pressure relief valve 4 is color coded with respect to the second color of the pressure gauge 3, and the high pressure relief valve 5 is color coded with respect to the third color of the pressure gauge 3. The users are also able to identify the proper functionality of the low pressure relief valve 4 and the high pressure relief valve 5 within the present invention, as the low pressure relief valve 4 opens when the pressure gauge 3 reaches the second color and the high pressure relief valve 5 opens when the pressure gauge 3 reaches the third color.

Figure 8:
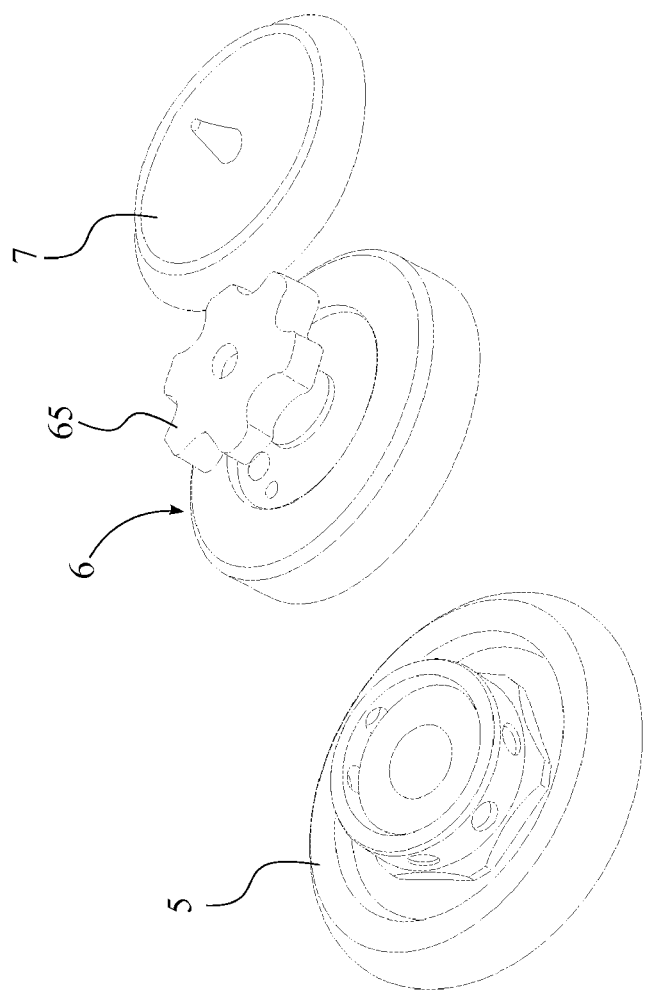
FIG. 8 is an outside view of the high pressure relief valve, the dump valve, and the auxiliary valve of the present invention.
Figure 12:
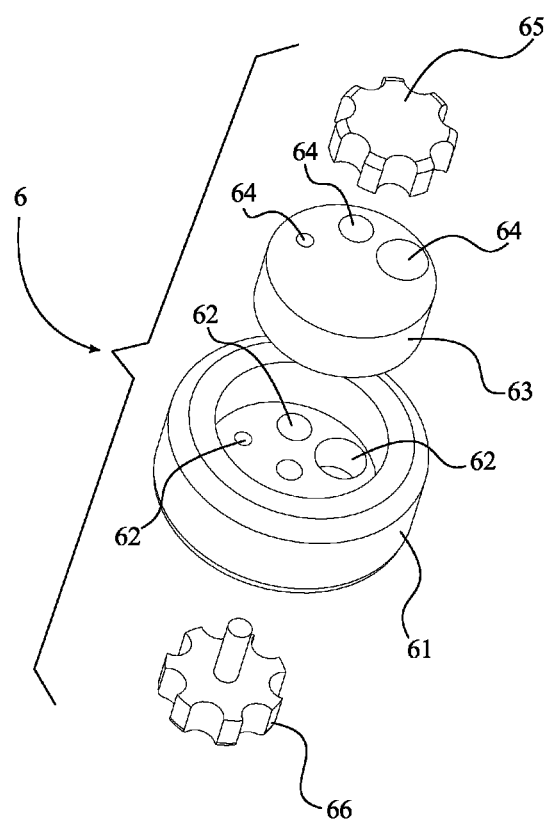
FIG. 12 is an exploded view of the dump valve of the present invention.

In reference to FIG. 1, FIG. 8 and FIG. 12, the dump valve 6 is externally connected to the collapsible lateral wall 11 in such way that the dump valve 6 is traversed through the collapsible lateral wall 11. The dump valve 6 allows the patient or a responsible individual to either control the inside pressure of the inflatable enclosure 1 or to deflate the inflatable enclosure 1. The dump valve 6 comprises a stationary plate 61, a plurality of stationary holes 62, a rotary plate 63, a plurality of rotary holes 64, an outside knob 65, and an inside knob 66. The stationary plate 61 is connected with the collapsible lateral wall 11, and the plurality of stationary holes 62 is radially positioned on the stationary plate 61. Each of the plurality of stationary holes 62 has a different diameter, where each of the plurality of stationary holes 62 differs from one another. The rotary plate 63 is rotatably connected with the stationary plate 61, where the rotary plate 63 is adjacently positioned with the stationary plate 61 from outside of the collapsible lateral wall 11. The plurality of rotary holes 64 is radially positioned on the rotary plate 63. Each of the plurality of rotary holes 64 has a different diameter, where each of the plurality of rotary holes 64 differs from one another. Since each of the plurality of stationary holes 62 and each of the plurality of rotary holes 64 have different diameters, The plurality of stationary holes 62 and the plurality of rotary holes 64 are positioned in the order of increasing size, such that a small hole is adjacent to a medium hole, the medium hole is in between the small hole and a large hole, and the large hole is adjacent to the medium hole. The outside knob 65 is concentrically connected with the rotary plate 63 and allows the individuals standing outside of the inflatable enclosure 1 to control inside pressure. The inside knob 66 is concentrically traversed through the stationary plate 61 and connected with the rotary plate 63 in such way that the inside knob 66 is oppositely positioned from the outside knob 65. The inside knob 66 allows a patient within the inflatable enclosure 1 to control the inside pressure without exiting the present invention.

Figure 9:
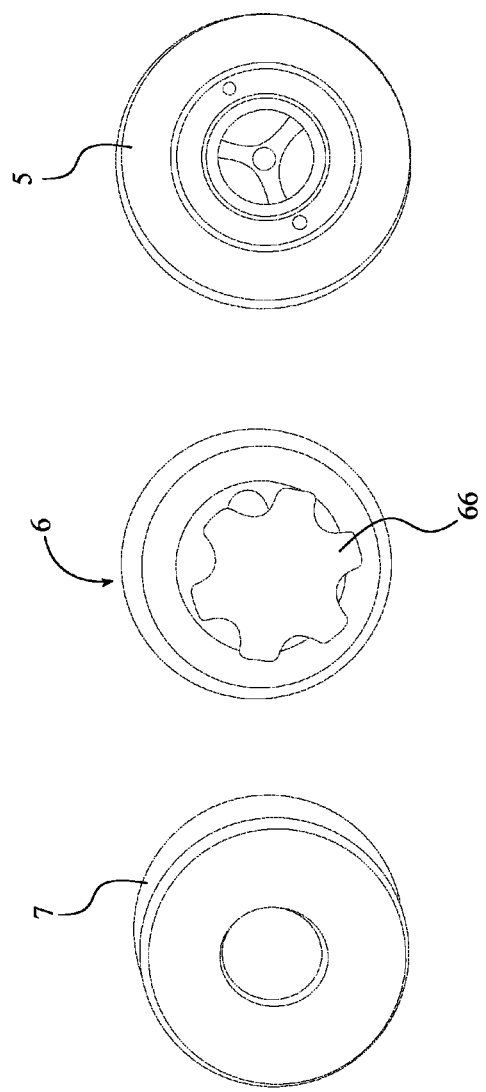
FIG. 9 is an inside view of the high pressure relief valve, the dump valve, and the auxiliary valve of the present invention.
Figure 10:
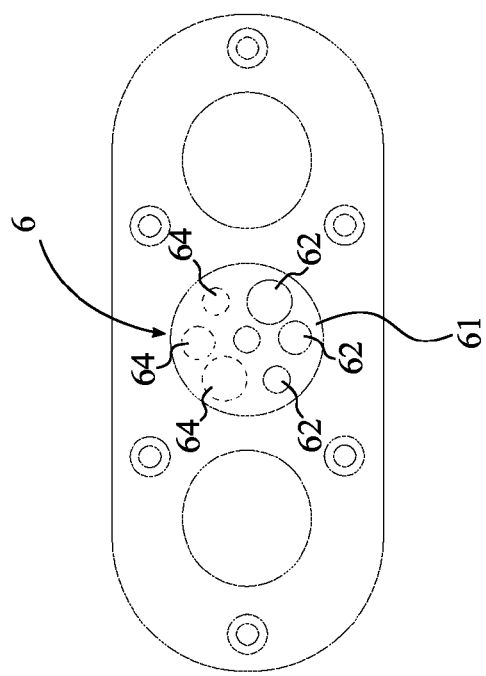
FIG. 10 is an inside view of the dump valve, showing the plurality of stationary holes and the plurality of rotary holes.

In reference to FIG. 9 and FIG. 10, the dump valve 6 is operated by turning the outside knob 65 or the inside knob 66 which turns the rotary plate 63, changing the alignment of the plurality of rotary holes 64 with respect to the plurality of stationary holes 62. As shown in FIG. 11-A, when none of the plurality of rotary holes 64 is aligned with the plurality of stationary holes 62, the dump valve 6 is completely sealed and the pressure inside the inflatable enclosure 1 remains constant. As shown in FIG. 11-D, when all of the plurality of rotary holes 64 is aligned with the plurality of stationary holes 62, the dump valve 6 is working at its full capacity. In reference to FIG. 11-B, FIG. 11-C, FIG. 11-E, and FIG. 11-F, by only aligning some of the plurality of rotary holes 64 with the plurality of stationary holes 62, the dump valve 6 can be used to adjust the rate of depressurization. In reference to FIG. 11-F, the first example that aligns some of the plurality of rotary holes 64 with the plurality of stationary holes 62 shows that the large hole of the plurality of stationary holes 62 is aligned with the small hole of the plurality of rotary holes 64, letting out a small amount of air, since the small hole of the plurality of rotary holes 64 bottlenecks the large hole of the plurality of stationary holes 62. In reference to FIG. 11-E, the second example that aligns some of the plurality of rotary holes 64 with the plurality of stationary holes 62 shows The large hole and the medium hole of the plurality of stationary holes 62 are aligned with the medium hole and the small hole of the plurality of rotary holes 64, which would release a larger amount of air. These two sample configurations allow some depressurization to occur, but not as much when compared to having all of the plurality of rotary holes 64 align with the plurality of stationary holes 62.

In reference to FIG. 8 and FIG. 9, the at least one auxiliary valve 7 is externally connected to the collapsible lateral wall 11 in such way that the at least one auxiliary valve 7 is traversed through the collapsible lateral wall 11. The at least one auxiliary valve 7 fluidly connects with any kind of standard medical device through a medical grade tube so that optional equipments can be fluidly connected with the present invention.

Figure 3:
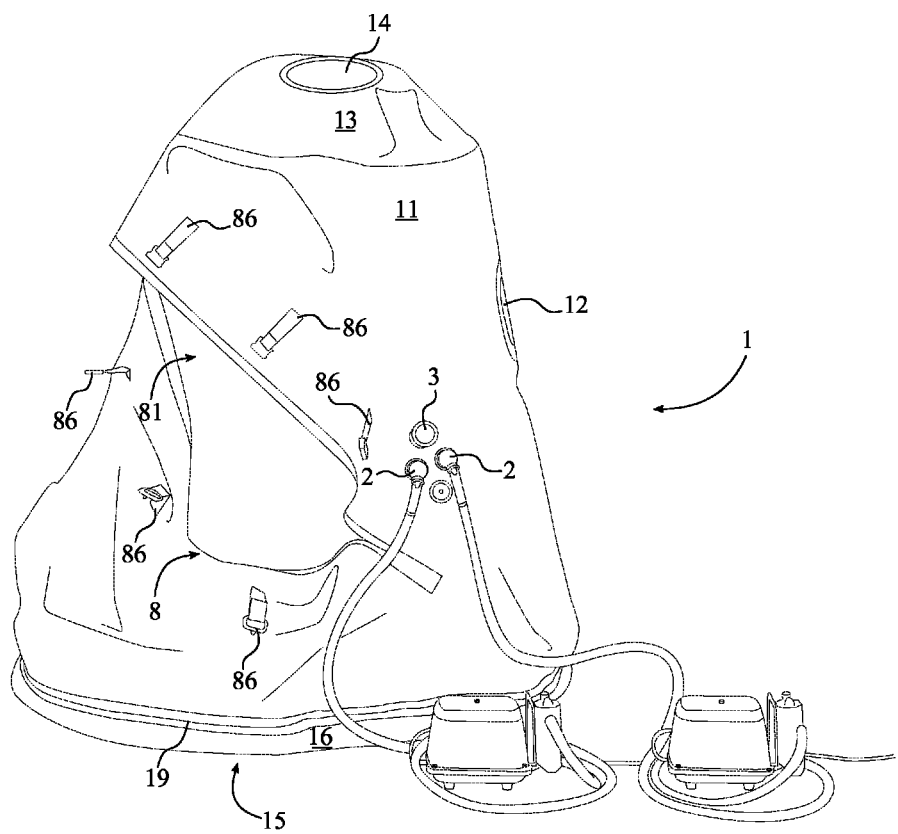
FIG. 3 is a front view of the preferred embodiment of the present invention with attached compressors, wherein the inflatable enclosure is not pressurized.
Figure 13:
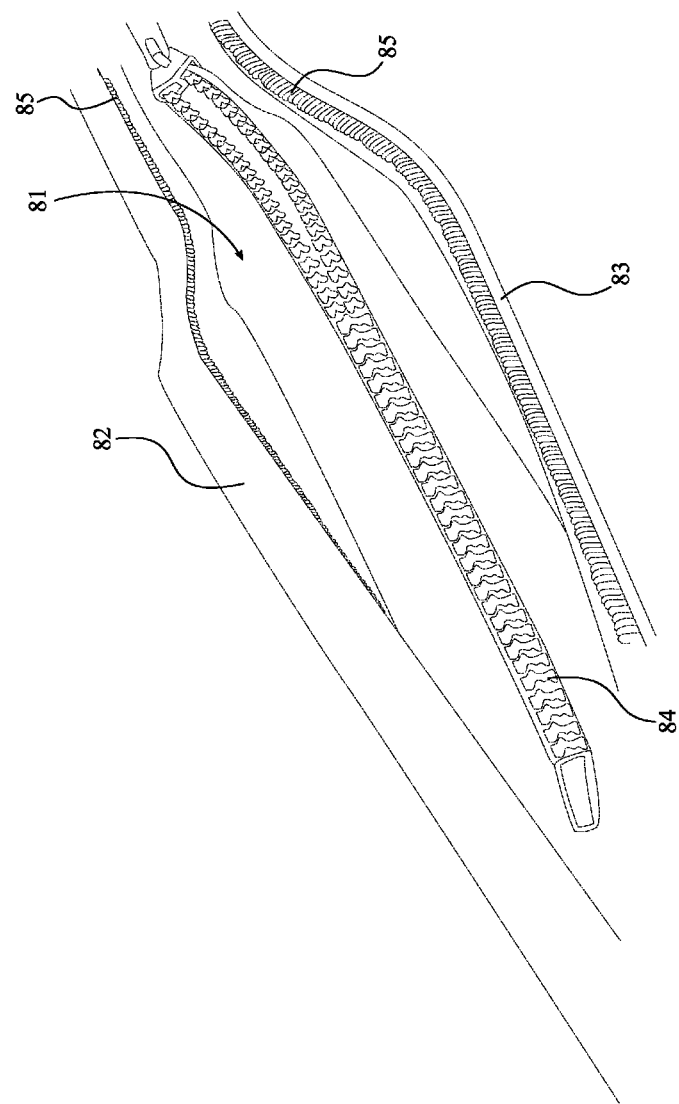
FIG. 13 is a detailed view of the access opening of the present invention.

In reference to FIG. 3 and FIG. 13, the access opening 8 comprises a slit 81, an inside zipper 84, an outside zipper 85, and a plurality of buckles 86. The access opening 8 is positioned on the collapsible lateral wall 11 and provides an opening so that the patients can move in and out of the inflatable enclosure 1. More specifically, the slit 81 that provides the opening comprises a first portion 82 and a second portion 83, where the first portion 82 and the second portion 83 are oppositely positioned from each other. The first portion 82 and the second portion 83 of the slit 81 are hermetically attached to each other through the inside zipper 84 so that the pressurized air can be withheld within the inflatable enclosure 1. The first portion 82 and the second portion 83 of the slit 81 are structurally attached to each other through the outside zipper 85 so that the present invention is able to maintain the structural integrity of the access opening 8. The structural strength of the access opening 8 is further improved as the first portion 82 and the second portion 83 of the slit 81 are structurally attached to each other through the plurality of buckles 86. The outside zipper 85 is adjacently positioned within the first portion 82 and the second portion 83, and the inside zipper 84 is adjacently positioned with the outside zipper 85 in such way that the inside zipper 84 is positioned within the collapsible lateral wall 11. The plurality of buckles 86 is adjacently positioned on the collapsible lateral wall 11 opposite from the inside zipper 84. For safety purposes, the inside zipper 84, the outside zipper 85, and the plurality of buckles 86 can be opened or closed from inside of the inflatable enclosure 1 or the outside of the inflatable enclosure 1.

In reference to FIG. 5, the inner carpet 9 is adjacently positioned on the rigid base 15 and within the collapsible lateral wall 11, where the inner carpet 9 provides additional protection to the base sleeve 16 while providing a comfortable flooring system for the patients. Since the inner carpet 9 is not permanently fixed to the rigid base 15, users can easily remove and insert the inner carpet 9 trough the access opening 8 without compromising the structural integrity of the present invention.

The internal frame 10 is adjacently positioned on the rigid base 15 and within the collapsible lateral wall 11 in such way that the internal frame 10 maintains the general shape of the present invention when the inflatable enclosure 1 is not pressurized allowing the patient to easily move in and out from the inflatable enclosure 1. Depending on different embodiments of the present invention, the internal frame 10 also differs so that the internal frame 10 is able to optimize its functionality with respect to the access opening 8.

Figure 14:
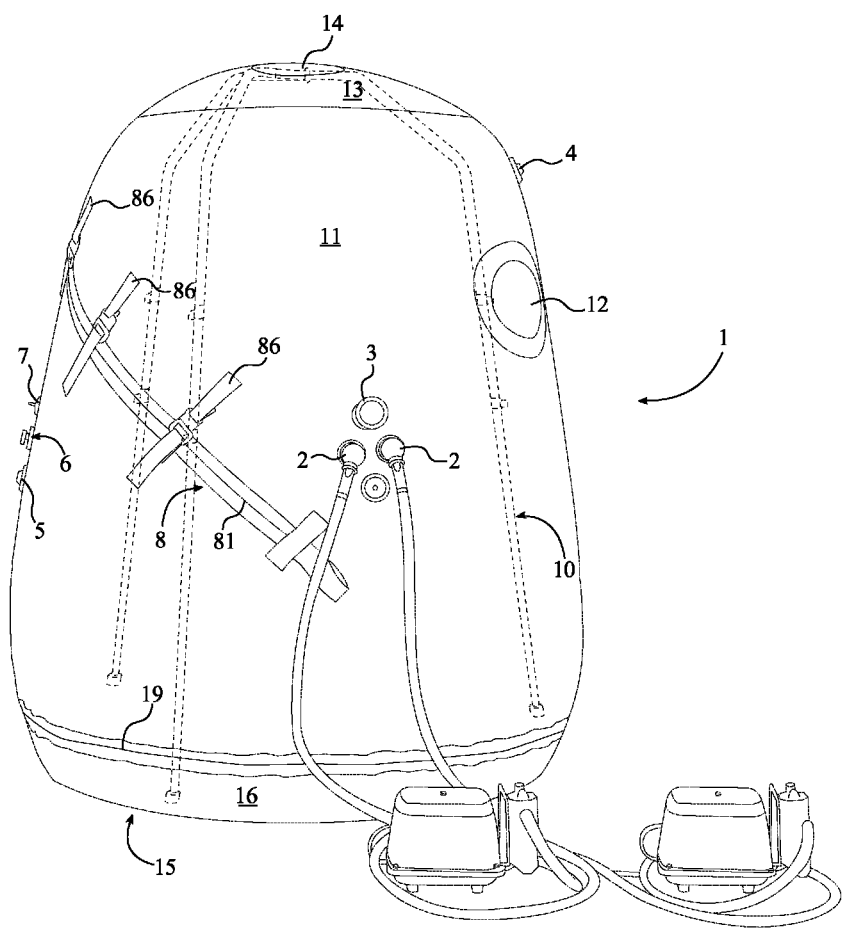
FIG. 14 is a perspective view of the internal frame within the preferred embodiment of the present invention, wherein the internal frame is shown with the dash lines.
Figure 15:
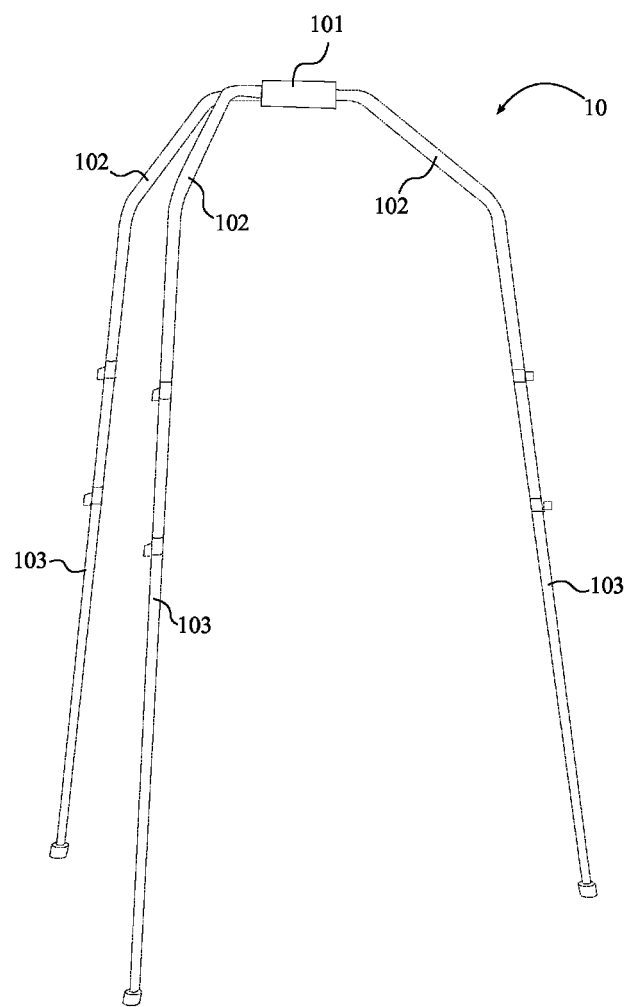
FIG. 15 is a perspective view of the internal frame of the preferred embodiment of the present invention.

In reference to FIG. 1 and FIG. 14, the preferred embodiment of the present invention, the slit 81 is diagonally positioned on the collapsible lateral wall 11 in between the roof panel 13 and the rigid base 15. The slit 81 of the preferred embodiment allows patients to move in and out from the inflatable enclosure 1 without any outside assistance. More specifically, patients can enter into and exit from the inflatable enclosure 1 through the diagonally positioned slit 81 and close the access opening 8 by themselves. In reference to FIG. 15, the internal frame 10 of the preferred embodiment comprises an arch connector 101, a plurality of arch poles 102, and a plurality of telescopic poles 103. Each of the plurality of arch poles 102 is removably attached to the arch connector 101 by a spring loaded mechanism. Additional locking screws of the arch connector 101 can further secure the plurality of arch poles 102 with the arch connector 101. Each of the plurality of telescopic poles 103 is removably attached with each of the plurality of arch poles 102 in such way that the plurality of arch poles 102 is positioned in between the arch connector 101 and the plurality of telescopic poles 103. The plurality of telescopic poles 103 allows the users to adjust the height of the internal frame 10 so that the internal frame 10 can securely positioned with the inflatable enclosure 1 with the correct height. More specifically, the arch connector 101 and the plurality of arch poles 102 are adjacently positioned with the roof panel 13, and the plurality of telescopic poles 103 is adjacently positioned on the rigid base 15 and within the collapsible lateral wall 11 in order to create a spaces environment for the patient.

Figure 16:
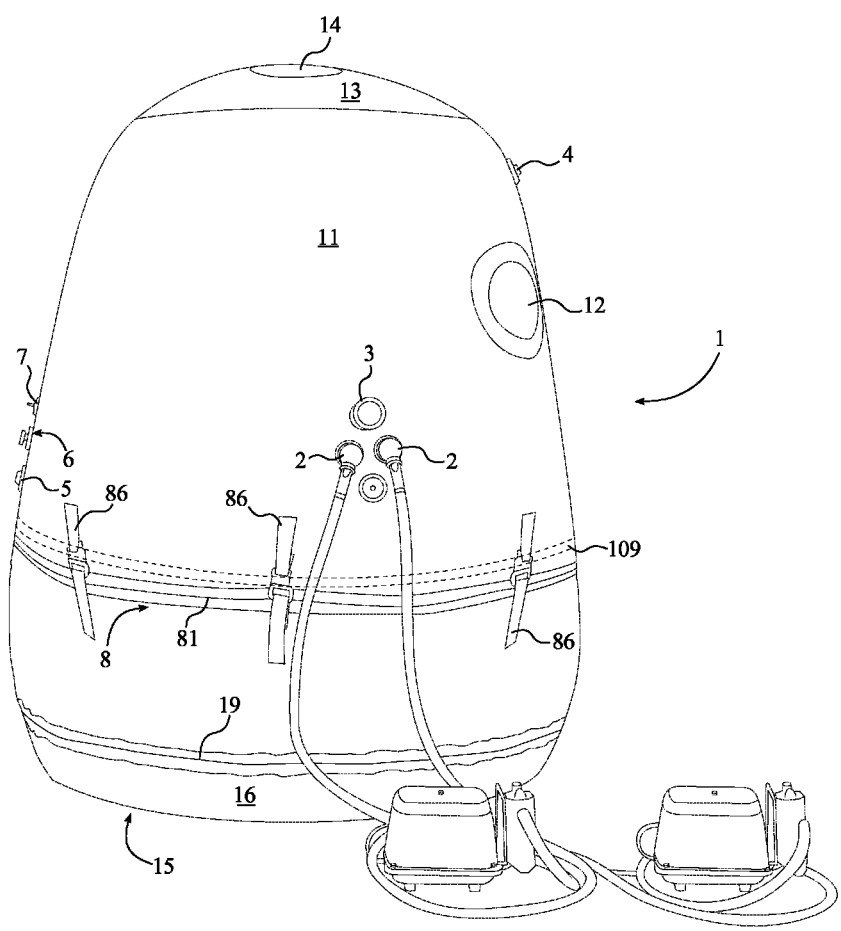
FIG. 16 is a perspective view of the alternative embodiment of the present invention with attached compressors, wherein the inflatable enclosure is pressurized.
Figure 17:
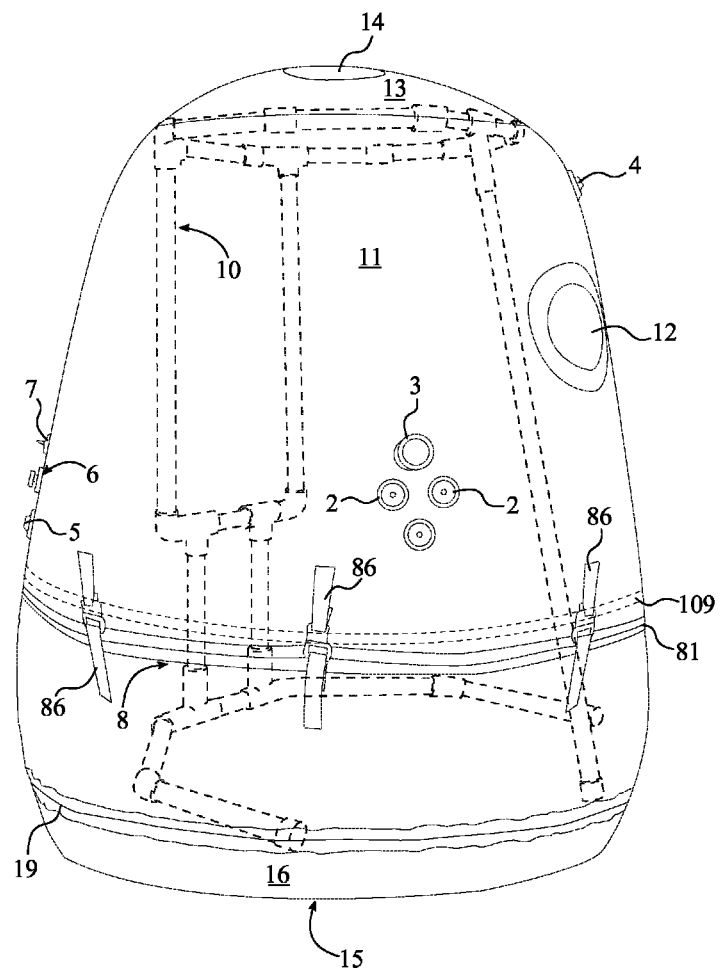
FIG. 17 is a perspective view of the internal frame within the alternative embodiment of the present invention, wherein the closed position of the internal frame is shown with the dash lines.
Figure 18:
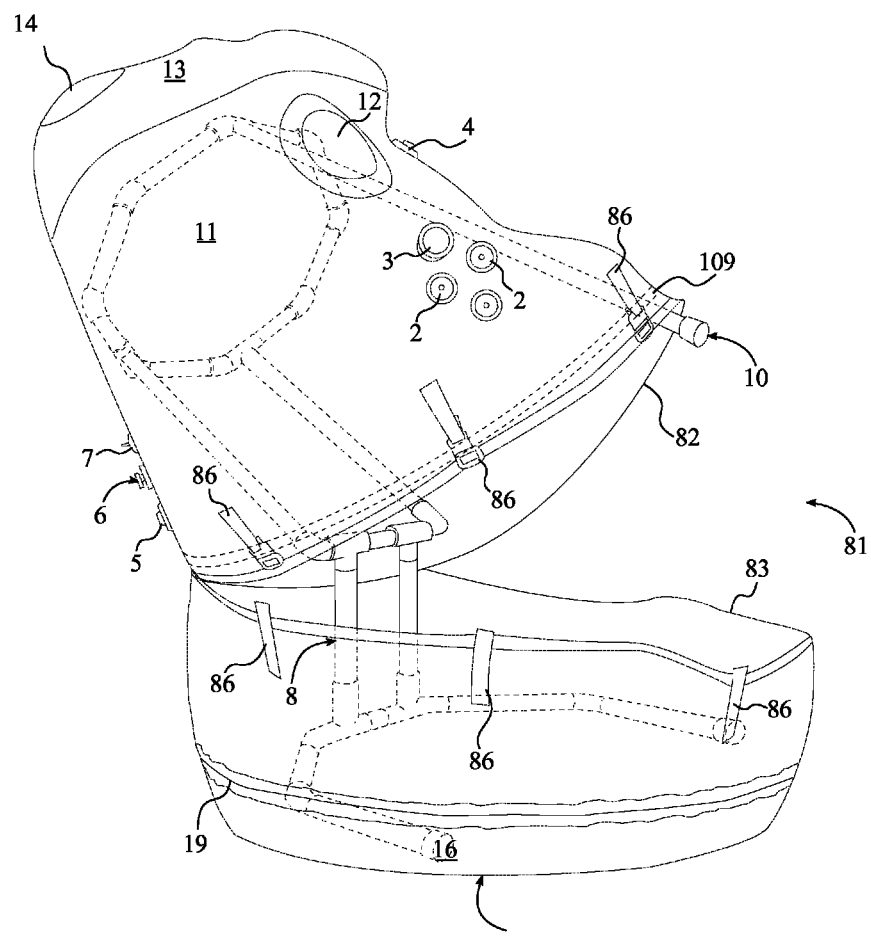
FIG. 18 is a perspective view of the internal frame within the alternative embodiment of the present invention, wherein the opened position of the internal frame is shown with the dash lines.
Figure 19:
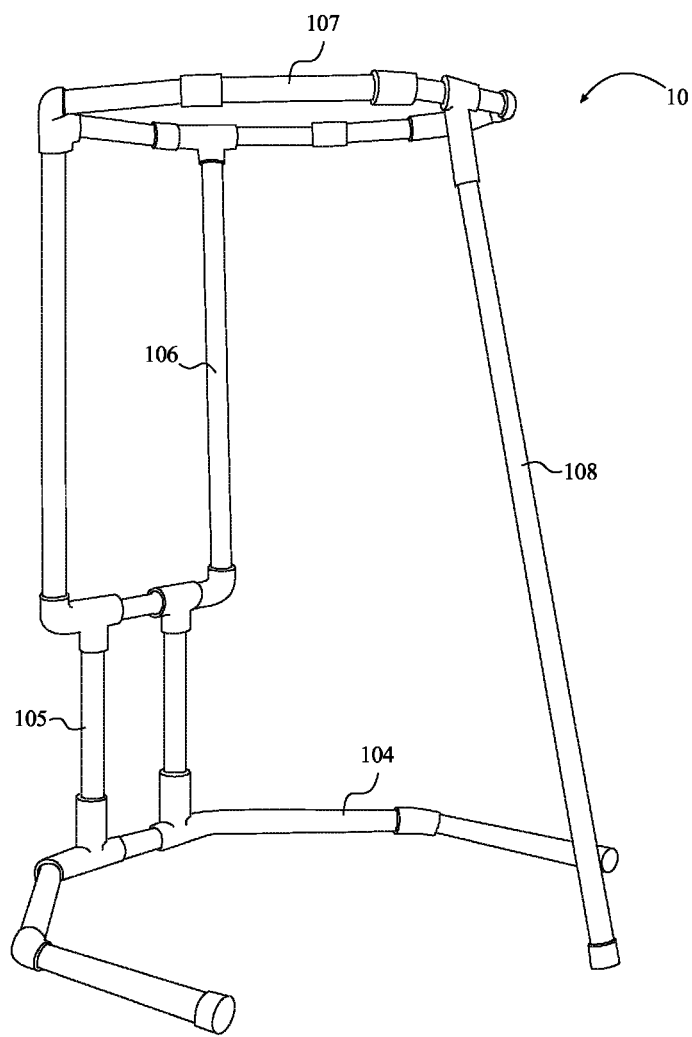
FIG. 19 is a perspective view of the internal frame of the alternative embodiment of the present invention in the closed position.
Figure 20:
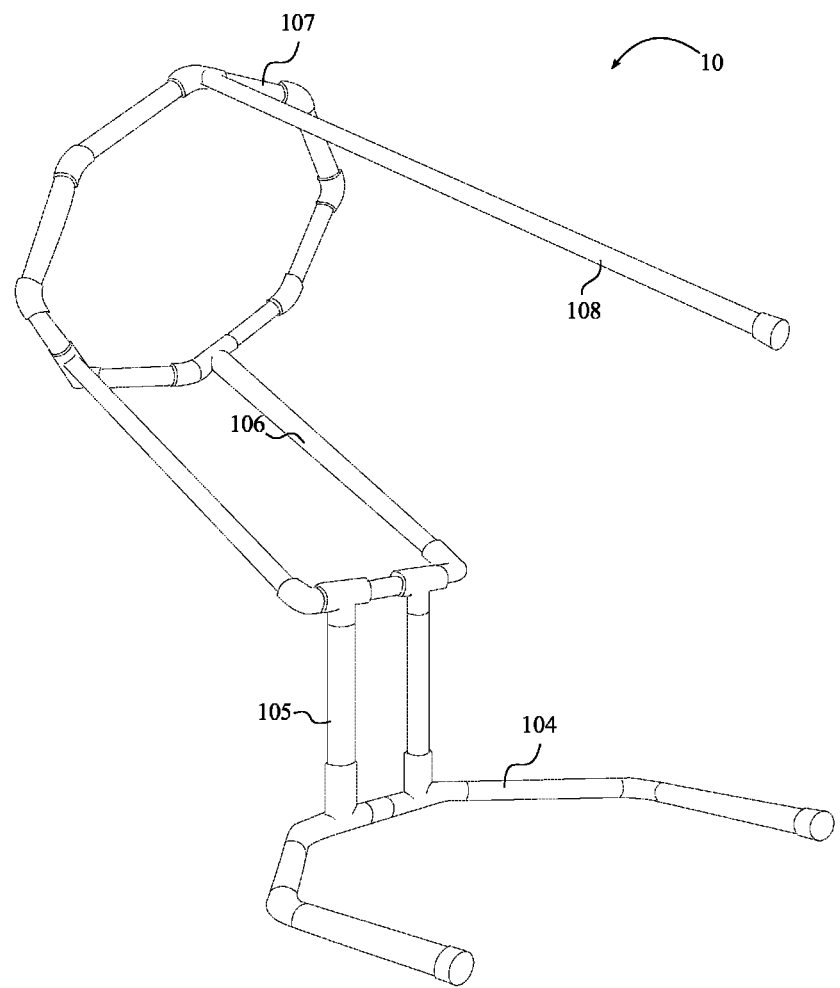
FIG. 20 is a perspective view of the internal frame of the preferred embodiment of the present invention in the opened position.

In reference to FIG. 16, FIG. 17, and FIG. 18, the alternative embodiment of the present invention, the slit 81 is circumferentially positioned around the collapsible lateral wall 11 adjacent to the rigid base 15. The alternative embodiment is configured in a way that a patient on a wheelchair is able to access the inflatable enclosure 1 with some outside assistance. The internal frame 10 of the alternative embodiment comprises a base frame 104, a fixed hinged post 105, a rotatable hinged post 106, a top frame 107, an upright post 108, and a lateral wall rim 109. As for the backside of the internal frame 10, the fixed hinged post 105 is perpendicularly attached with the base frame 104, and the rotatable hinged post 106 is pivotally attached with the fixed hinged post 105 opposite from the base frame 104, where the base frame 104 is adjacently positioned on the rigid base 15 and the fixed hinged post 105 and the rotatable hinged post 106 are positioned within the collapsible lateral wall 11. The top frame 107 is perpendicularly attached with the rotatable hinged post 106 opposite from the fixed hinged post 105, where the top frame 107 is adjacently positioned with the roof panel 13. As for the front side of the internal frame 10, the upright post 108 is attached with the top frame 107 opposite from the fixed hinged post 105 and the rotatable hinged post 106 in such way that the upright post 108 extends from the top frame 107 to the base frame 104. The upright post 108 is positioned on the rigid base 15 and within the collapsible lateral wall 11. The internal frame 10 can pivot within the fixed hinged post 105 and the rotatable hinged post 106 so that the internal frame 10 can be switched in between a closed position and an opened positioned. In reference to FIG. 18 and FIG. 20, the opened position of the internal frame 10 allows the separation of the first portion 82 and the second portion 83 of the slit 81 so that the wheelchair can be pushed into and pulled from the inflatable enclosure 1 through the circumferentially positioned slit 81. When the upright post 108 is lifted within the inflatable enclosure 1, the first portion 82 of the slit 81 along with the top part of the collapsible lateral wall 11 is moved away from the rigid base 15 and the second portion 83 so that the access opening 8 can be opened. Then the second portion 83 of the slit 81 is rolled downward and a carpet is placed over the second portion 83 so that the lateral wall 11 and the access opening 8 is not damage by the wheelchair as the wheelchair is moved in and out from the inflatable enclosure 1. The lateral wall rim 109 is inserted within the collapsible lateral wall 11 adjacent to the slit 81, preferably adjacent to the first portion 82, so that the overall shape of the alternative embodiment is not compromised during the separating of the first portion 82 and the second portion 83. In reference to FIG. 17 and FIG. 19, once the wheelchair is positioned within the inflatable enclosure 1, the internal frame 10 is switched into the closed positioned so that the access opening 8 can be closed.

Although the invention has been explained in relation to its preferred embodiment, it is to be understood that many other possible modifications and variations can be made without departing from the spirit and scope of the invention as hereinafter claimed.

What is claimed is:
1. A portable hyperbaric chamber with a vertical mounting system comprises:
    an inflatable enclosure;
    a plurality of fill valves;
    a pressure gauge;
    a low pressure relief valve;
    a high pressure relief valve;
    a dump valve;
    at least one auxiliary valve;
    an access opening;
    an inner carpet;
    an internal frame;
    wherein the inflatable enclosure comprises a collapsible lateral wall, a roof panel, and a rigid base;
    the access opening comprises a slit, an inside zipper, an outside zipper, and a plurality of buckles;
    wherein the slit is circumferentially positioned around the collapsible lateral wall adjacent to the rigid base;
    the internal frame comprises a base frame, a fixed hinged post, a rotatable hinged post, top frame, an upright post, and a lateral wall rim;
    the fixed hinged post is perpendicularly attached with the base frame;
    the rotatable hinged post is pivotally attached with the fixed hinged post opposite from the base frame;
    the top frame is perpendicularly attached with the rotatable hinged post opposite from the fixed hinged post;
    the upright post is attached with the top frame opposite from the fixed hinged post and the rotatable hinged post;
    the lateral wall rim is inserted within the collapsible lateral wall adjacent to the slit;
    the base frame is adjacently positioned on the rigid base;
    the fixed hinged post and the rotatable hinged post is positioned within the collapsible lateral wall;
    the top frame is adjacently positioned with the roof panel; and the upright post is positioned within the collapsible lateral wall.

2. The portable hyperbaric chamber with a vertical mounting system as claimed in claim 1 comprises:
the roof panel comprises a first transparent window;
the collapsible lateral wall comprises a second transparent window;
the first transparent window being concentrically positioned on the roof panel;
the second transparent window being positioned on the collapsible lateral wall;
the collapsible lateral wall being perimetrically connected around the rigid base and the roof panel; and
the collapsible lateral wall being positioned in between the rigid base and the roof panel.

3. The portable hyperbaric chamber with a vertical mounting system as claimed in claim 1 comprises:
the rigid base comprises a base sleeve, a floor, and a rim;
the rim being perimetrically connected around the floor;
the floor and the rim being removably positioned within the base sleeve through a base opening; and
the floor and the rim being concentrically positioned with the base sleeve.

4. The portable hyperbaric chamber with a vertical mounting system as claimed in claim 1 comprises:
the plurality of fill valves being connected and traversing through the collapsible lateral wall;
each of the plurality of fill valves being fluidly connected with a compressor;
the pressure gauge being connected to and traversing through the collapsible lateral wall;
the low pressure relief valve being connected to and traversing through the collapsible lateral wall;
the high pressure relief valve being connected to and traversing through the collapsible lateral wall;
the dump valve being connected to and traversing through the collapsible lateral wall; and
the at least one auxiliary valve being connected to and traversing through the collapsible lateral wall.

5. The portable hyperbaric chamber with a vertical mounting system as claimed in claim 4 comprises:
the dump valve comprises a stationary plate, a plurality of stationary holes, a rotary plate, a plurality of rotary holes, an outside knob, and an inside knob;
the stationary plate being connected with the collapsible lateral wall;
the plurality of stationary holes being radially positioned on the stationary plate;
the rotary plate being rotatably connected with the stationary plate;
the rotary plate being adjacently positioned with the stationary plate outside the collapsible lateral wall;
the plurality of rotary holes being radially positioned on the rotary plate;
the outside knob being concentrically connected with the rotary plate;
the outside knob being oppositely positioned from the stationary plate;
the inside knob being concentrically traversing through the stationary plate and connected with the rotary plate; and
the inside knob being oppositely positioned from the outside knob and within the collapsible lateral wall.

6. The portable hyperbaric chamber with a vertical mounting system as claimed in claim 1 comprises:
the slit being positioned on the collapsible lateral wall;
the slit comprises a first portion and a second portion;
the first portion and the second portion being oppositely positioned from each other;
the first portion and the second portion being hermetically attached to each other through the inside zipper;
the first portion and the second portion being structurally attached to each other through the outside zipper;
the first portion and the second portion being structurally attached to each other through the plurality of buckles;
the outside zipper being adjacently positioned within the first portion and the second portion;
the inside zipper being positioned within the collapsible lateral wall; and
the plurality of buckles being oppositely positioned from the inside zipper and adjacently positioned on the collapsible lateral wall.

7. The portable hyperbaric chamber with a vertical mounting system as claimed in claim 1 comprises:
the inner carpet being adjacently positioned with the rigid base and within the collapsible lateral wall; and
the internal frame being adjacently positioned on the rigid base and within the collapsible lateral wall.

8. A portable hyperbaric chamber with a vertical mounting system comprises:
an inflatable enclosure;
a plurality of fill valves;
a pressure gauge;
a low pressure relief valve;
a high pressure relief valve;
a dump valve;
at least one auxiliary valve;
an access opening;
an inner carpet;
an internal frame;
wherein the inflatable enclosure comprises a collapsible lateral wall, a roof panel, and a rigid base;
the access opening comprises a slit, an inside zipper, an outside zipper, and a plurality of buckles;
the collapsible lateral wall comprises a second transparent window;
the roof panel comprises a first transparent window;
the rigid base comprises a base sleeve, a floor, and a rim;
the first transparent window being concentrically positioned on the roof panel;
the second transparent window being positioned on the collapsible lateral wall;
the collapsible lateral wall being perimetrically connected around the rigid base and the roof panel;
the collapsible lateral wall being positioned in between the rigid base and the roof panel;
the rim being perimetrically connected around the floor;
the floor and the rim being removably positioned within the base sleeve through a base opening;
the floor and the rim being concentrically positioned with the base sleeve;
wherein the slit is circumferentially positioned around the collapsible lateral wall adjacent to the rigid base;
the internal frame comprises a base frame, a fixed hinged post, a rotatable hinged post, top frame, an upright post, and a lateral wall rim;
the fixed hinged post is perpendicularly attached with the base frame;
the rotatable hinged post is pivotally attached with the fixed hinged post opposite from the base frame;
the top frame is perpendicularly attached with the rotatable hinged post opposite from the fixed hinged post;

the upright post is attached with the top frame opposite from the fixed hinged post and the rotatable hinged post;

the lateral wall rim is inserted within the collapsible lateral wall adjacent to the slit;

the base frame is adjacently positioned on the rigid base;

the fixed hinged post and the rotatable hinged post is positioned within the collapsible lateral wall;

the top frame is adjacently positioned with the roof panel; and the upright post is positioned within the collapsible lateral wall.

9. The portable hyperbaric chamber with a vertical mounting system as claimed in claim 8 comprises:

the plurality of fill valves being connected and traversing through the collapsible lateral wall;

each of the plurality of fill valves being fluidly connected with a compressor;

the pressure gauge being connected to and traversing through the collapsible lateral wall;

the low pressure relief valve being connected to and traversing through the collapsible lateral wall;

the high pressure relief valve being connected to and traversing through the collapsible lateral wall;

the dump valve being connected to and traversing through the collapsible lateral wall; and the at least one auxiliary valve being connected to and traversing through the collapsible lateral wall.

10. The portable hyperbaric chamber with a vertical mounting system as claimed in claim 9 comprises:

the dump valve comprises a stationary plate, a plurality of stationary holes, a rotary plate, a plurality of rotary holes, an outside knob, and an inside knob;

the stationary plate being connected with the collapsible lateral wall;

the plurality of stationary holes being radially positioned on the stationary plate;

the rotary plate being rotatably connected with the stationary plate;

the rotary plate being adjacently positioned with the stationary plate outside the collapsible lateral wall;

the plurality of rotary holes being radially positioned on the rotary plate;

the outside knob being concentrically connected with the rotary plate;

the outside knob being oppositely positioned from the stationary plate;

the inside knob being concentrically traversing through the stationary plate and connected with the rotary plate; and the inside knob being oppositely positioned from the outside knob and within the collapsible lateral wall.

11. The portable hyperbaric chamber with a vertical mounting system as claimed in claim 8 comprises:

the slit being positioned on the collapsible lateral wall;

the slit comprises a first portion and a second portion;

the first portion and the second portion being oppositely positioned from each other;

the first portion and the second portion being hermetically attached to each other through the inside zipper;

the first portion and the second portion being structurally attached to each other through the outside zipper;

the first portion and the second portion being structurally attached to each other through the plurality of buckles;

the outside zipper being adjacently positioned within the first portion and the second portion;

the inside zipper being positioned within the collapsible lateral wall; and the plurality of buckles being oppositely positioned from the inside zipper and adjacently positioned on the collapsible lateral wall.

12. The portable hyperbaric chamber with a vertical mounting system as claimed in claim 8 comprises:

the inner carpet being adjacently positioned with the rigid base and within the collapsible lateral wall; and the internal frame being adjacently positioned on the rigid base and within the collapsible lateral wall.

\* \* \* \* \*